United States Patent [19]

White

[11] Patent Number: 5,713,661

[45] Date of Patent: Feb. 3, 1998

[54] HOCKEY PUCK SHAPED CONTINUOUS DIFFUSE ILLUMINATION APPARATUS AND METHOD

[75] Inventor: Timothy Peter White, New Boston, N.H.

[73] Assignee: Northeast Robotics, Inc., Weare, N.H.

[21] Appl. No.: 546,779

[22] Filed: Oct. 23, 1995

[51] Int. Cl.⁶ .................................................. F24V 11/00
[52] U.S. Cl. ........................... 362/355; 362/17; 362/362; 359/629
[58] Field of Search .................................. 362/8, 11, 16, 362/17, 355, 362, 307; 348/131; 359/583, 599, 629

[56] References Cited

U.S. PATENT DOCUMENTS

| | | |
|---|---|---|
| 2,792,740 | 5/1957 | Haynes . |
| 2,926,559 | 3/1960 | Oppenheimer . |
| 2,934,601 | 4/1960 | Oppenheimer . |
| 3,322,487 | 5/1967 | Renner . |
| 3,558,894 | 1/1971 | Odone et al. . |
| 3,596,083 | 7/1971 | Lovering . |
| 3,944,336 | 3/1976 | Carr, Jr. . |
| 3,984,157 | 10/1976 | LeVantine . |
| 3,985,425 | 10/1976 | Clapp . |
| 4,067,026 | 1/1978 | Pappanikolaou . |
| 4,139,306 | 2/1979 | Norton . |
| 4,185,902 | 1/1980 | Plaot . |
| 4,341,449 | 7/1982 | Iwata et al. . |
| 4,555,635 | 11/1985 | Yoshida . |
| 4,561,722 | 12/1985 | Smetana . |
| 4,601,576 | 7/1986 | Galbraith . |
| 4,677,473 | 6/1987 | Okamoto et al. ............... 348/131 |
| 4,691,231 | 9/1987 | Fitzmorris et al. . |
| 4,712,889 | 12/1987 | Schindl . |
| 4,735,497 | 4/1988 | Elterman ........................ 359/629 |
| 4,791,534 | 12/1988 | Lindberg . |
| 4,816,686 | 3/1989 | Hara et al. . |
| 4,854,688 | 8/1989 | Hayford et al. . |
| 4,877,326 | 10/1989 | Chadwick et al. . |
| 4,882,498 | 11/1989 | Cochran et al. . |
| 4,965,665 | 10/1990 | Amir . |
| 4,972,093 | 11/1990 | Cochran et al. . |
| 4,991,947 | 2/1991 | Sander et al. . |
| 5,011,265 | 4/1991 | Tamamura et al. . |
| 5,039,868 | 8/1991 | Kobayashi et al. . |
| 5,051,825 | 9/1991 | Cochran et al. . |
| 5,060,065 | 10/1991 | Wasserman . |
| 5,064,291 | 11/1991 | Reiser . |
| 5,072,127 | 12/1991 | Cochran et al. . |
| 5,155,558 | 10/1992 | Tannenbaum et al. . |
| 5,172,005 | 12/1992 | Cochran et al. . |
| 5,187,611 | 2/1993 | White et al. . |
| 5,461,417 | 10/1995 | White et al. . |
| 5,539,485 | 7/1996 | White . |
| 5,604,550 | 2/1997 | White . |

*Primary Examiner*—Y My Quach
*Attorney, Agent, or Firm*—Davis and Bujold

[57] ABSTRACT

The method and apparatus for providing a continuous, uniformed, diffused light environment for use in conjunction with an electronic machine vision or manual microscope inspection system, particularly for inspection of specular surfaces such as ball bearings, reflective packaging and other shiny surfaces. The illumination device includes a source of light which is associated with at least the secondary diffusers to provide secondary diffused illumination, of an object to be observed, substantially along the observation axis of the object. The same light source may also illuminate a rear surface of the primary diffuser. The height of the illumination device is approximately three and one-half times the clear aperture dimension of the illumination device or less. The illumination devices is arranged to provide uniformed illumination of the object with light which is equal in intensity and character to facilitate accurately viewing of the entire area of the object to be viewed.

20 Claims, 9 Drawing Sheets

HOCKEY PUCK SHAPED CONTINUOUS DIFFUSE ILLUMINATION APPARATUS AND METHOD

FIELD OF THE INVENTION

The invention pertains to a method and apparatus for permitting electronic machine vision of light reflecting objects wherein a true observation of the surface being viewed is obtained by masking potential reflections resulting along the observation axis due to observation windows and cameras, or other non-illuminating discontinuities in the illumination environment.

DESCRIPTION OF THE RELATED ART

Electronic machine vision apparatus is commonly employed in conjunction with automatic machining, assembly and inspection apparatus, particularly of the robotics type. Television cameras are commonly employed to observe the object being machined, assembled, or inspected, and the signal received and transmitted by the camera can be compared to a standard signal or database to determine if the observed article is properly machined, oriented, and/or assembled. Also, machine vision apparatus is widely used in inspection and flaw detection applications whereby inconsistencies and imperfection in both hard and soft goods can be rapidly ascertained and adjustments or rejections instantaneously effected.

Machine vision apparatus detects abnormalities by comparing the signal generated by the camera with a predetermined signal indicating proper dimensions, appearance, orientation, or the like. In order to achieve consistent and accurate results when using machine vision apparatus employing electronic cameras, it is very important that consistent and uniform lighting of the observed object occur, as the lighting will seriously affect the vision signal generated and produce irregular signals even though no fault may exist in the object being observed other than it is not uniformly illuminated.

Illumination problems in machine vision applications are particularly present when the object being observed has a shiny specular surface. For instance, in the inspection of soldered circuits such as used with printed circuit boards the highly reflective nature and uneven surface geometry of the solder makes it very difficult to obtain an accurate electronic signal, and the same is true when machine vision inspecting ball bearings, reflective packaging, and other objects having shiny surfaces or areas, particularly irregular shiny surfaces.

When utilizing machine vision techniques and apparatus in shiny surface applications, it is common to employ complicated lighting systems for illuminating the object being observed, and it is a purpose of such lighting systems to eliminate shadows, highlights, underlights, reflections and other lighting characteristics caused by shiny convex surface objects. An illumination device which achieves many of the objects of the present invention is disclosed in a related patent of the Inventor, namely, U.S. Pat. No. 5,461,417 issued Oct. 24, 1995. That patent discloses a device which provides a first source of primary diffused light which illuminates a major portion of the object to be observed, except for a portion effected by the opening and a second source of diffused light provided along the observation axis to illumination the portion of the object effected by the opening. One of the major drawbacks associated with such device is that it is relatively large and bulky and the design is not readily adapted for miniaturization due to its geometry.

OBJECTION OF THE INVENTION

Wherefore, it is an object of the present invention to overcome the above noted disadvantages of the illumination devices currently available.

It is an object of the invention to provide a method and apparatus for illuminating an object to be observed by machine vision cameras wherein a diffused illumination of the object is produced which is continuous in nature and is free of dark or void portions capable of generating erroneous vision signals.

Another object of the invention is to provide a method and apparatus for illuminating specular objects to be observed by electronic machine vision cameras, film cameras, or human observers, wherein the object is uniformly illuminated by a primary, off-observation axis source of diffused light emitting from surface adjacent the object, having an observation window or viewing orifice to permit vision along an observation axis that is masked against reflection by the object.

Another object of the invention is to provide a method and apparatus for illuminating specular objects to be observed by electronic machine vision cameras wherein the object is illuminated by diffused light emitted from an off-observation axis diffuse light source of a shape and size sufficient to provide substantially uniform illumination over the entire surface of the object to be observed while also supplying diffused light along the observation axis through an observation window to permit accurate vision along an observation axis.

Yet another object of the invention is to provide a method and apparatus which supplies diffused light along the observation axis of an intensity and character substantially equal to the intensity and character of the primary diffused light illuminating the object while facilitating miniaturization of the illumination device.

Still another object of the invention is to provide an illumination device which is very compact in size and occupies a volume of between about 0.5 to 30 cubic inches, or possibly smaller.

A still further object of the invention is to form the first and second diffusers from a single monolithic component so that the height of the illumination device is approximately equal to a clear aperture dimension of the illumination device and the width or diameter of the illumination device is approximately three (3) times the clear aperture dimension.

A still further object of the invention is to calibrate the primary diffuser surface, prior to use, to ensure uniformed illumination by the primary diffuser surface of the object to be observed Yet a further object of the invention is to minimize the height of the light source assembly by utilizing a curved beam splitter.

A further object of the invention is, in one embodiment, to utilize a single light source to illuminate both the primary and the secondary diffusers so that the single light provides both the off axis diffuse illumination as well as the diffuse illumination provided along the observation axis.

Still another object of the invention is to provide a compact illumination device which is compact in size and has a camera incorporated therein.

SUMMARY OF THE INVENTION

The invention relates to a compact diffuse lighting device for evenly illuminating a desired portion of an object when observed along an observing axis extending through an object observing location, said diffuse illumination device comprising a first diffuser surface, for supplying diffused light, defining an opening through which the observing axis passes, said first diffuser surface being arranged to supply a primary diffused light to provide said even illumination of the desired portion of the object, when placed at the observing location and viewed along said observing axis, except for a portion of the object effected by the opening; a light source for supplying secondary diffused light to illuminate a desired portion of the object; and a partially reflective mirror for supplying said secondary diffused light along the observing axis to evenly illuminate each portion of the object effected by the opening to produce, when a primary diffused light illuminates said surface, said even illumination of the object when viewed along the observing axis; wherein said light source for supply secondary diffused light is located adjacent said first diffuser surface for supplying said primary diffused light.

The invention also relates to a method of evenly illuminating a desired portion of an object to be observed, when observed along an observing axis extending through an object observing location, via a compact diffuse lighting device, said method comprising the steps of supplying diffused light, via a first diffuser surface defining an opening through which the observing axis passes, and arranging said first diffuser surface to supply a primary diffused light to provide said even illumination of the desired portion of the object, when placed at the observing location and viewed along said observing axis, except for a portion of the object effected by the opening; supplying secondary diffused light, via a light source, to illuminate a desired portion of the object; and using a partially reflective mirror to supply said secondary diffused light along the observing axis to evenly illuminate each portion of the object effected by the opening to produce, when a primary diffused light illuminates said surface, said even illumination of the object when viewed along the observing axis; and locating said light source, for supply secondary diffused light, adjacent said first diffuser surface for also supplying said primary diffused light.

As will be appreciated from the following description, the method and apparatus permitting the practice of the invention is relatively simple and inexpensive as compared with prior art devices incapable of providing a true continuous diffused light as provided by the invention.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Turning now to FIGS. 1—8, a first embodiment of the present invention will now be described in detail. This embodiment is a compacted illumination device having a height to width ratio of about 1:3, i.e. a height of approximately 1 inch and a diameter of approximately 3 inches. The compact illumination device 2 comprises an exterior housing 4 which comprises a substantially planar top wall 3 and a substantially cylindrical side wall 5 which are connected to one another by a small radius curved transition to form a unitary monolithic structure. The end of the exterior housing 4 opposite the top wall 3 is an open end which, prior to use, is covered by an outer diffuser 10. An observation device 1, such as a camera, a human observer, or some other suitable observation device is positioned along the observation axis A at a location remote from the object O to be observed with the compact illumination device 2 positioned between the observation device 1 and the object O to be observed.

Figure 2:
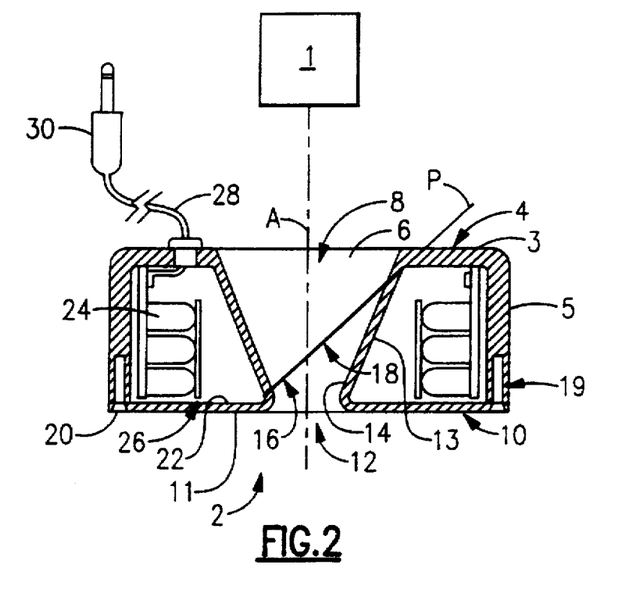
FIG. 2 is a diagrammatic cross-sectional view to a first embodiment of the illumination device according to the present invention.
Figure 3:
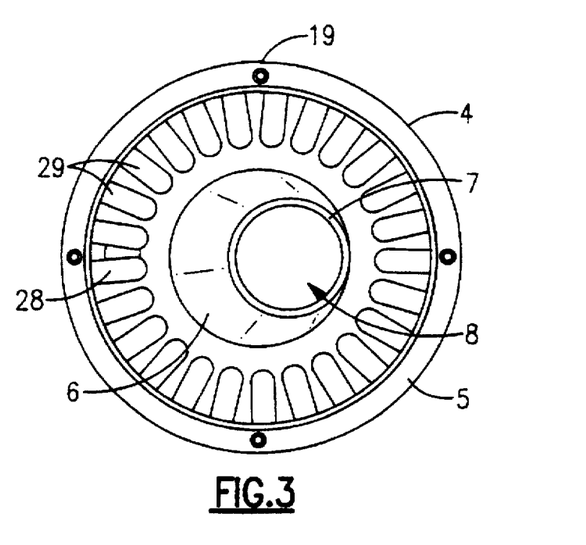
FIG. 3 is a bottom plan view of the illumination device of FIG. 2 prior to attachment of the diffuser component.
Figure 4:
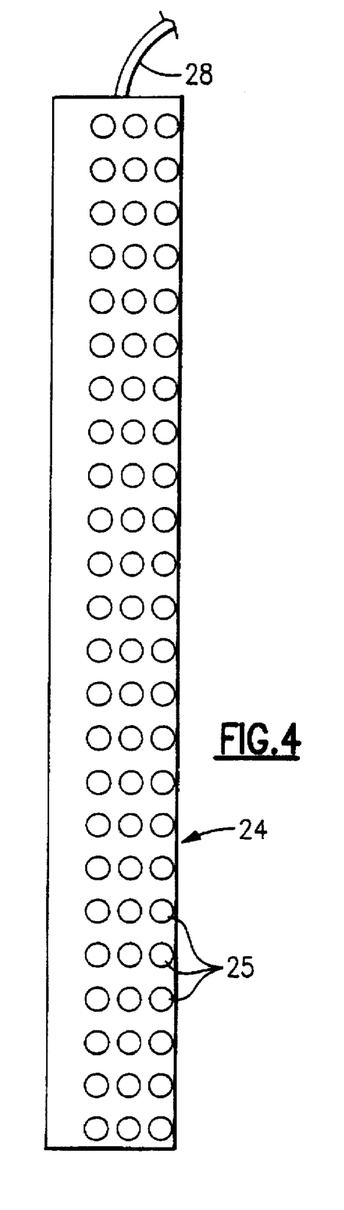
FIG. 4 is a diagrammatic plan view of a flexible circuit containing a plurality of high intensity LEDs.
Figure 5:
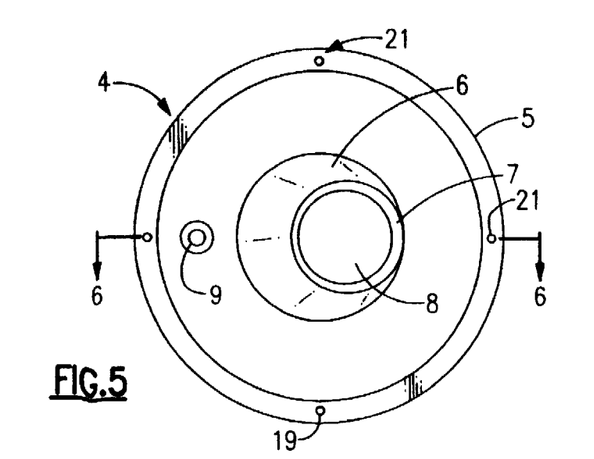
FIG. 5 is a bottom plan view of the exterior housing of FIG. 2.
Figure 6:
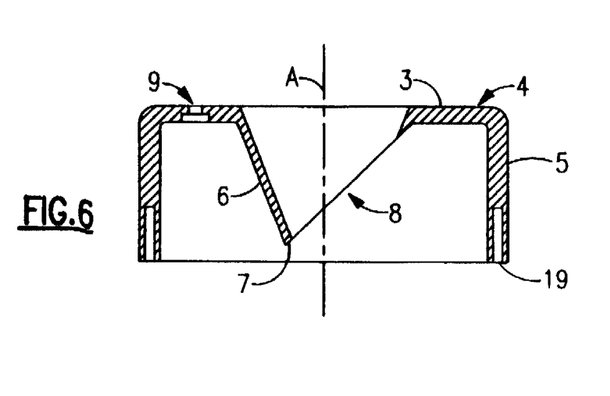
FIG. 6 is a cross-sectional view of the exterior housing along section line 6—6 of FIG. 5.
Figure 7:
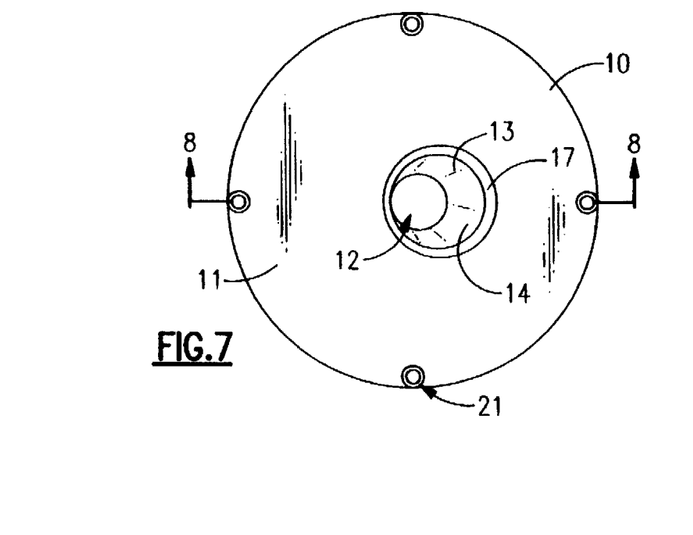
FIG. 7 is a top plan view of the diffuser component shown in FIG. 2.
Figure 8:
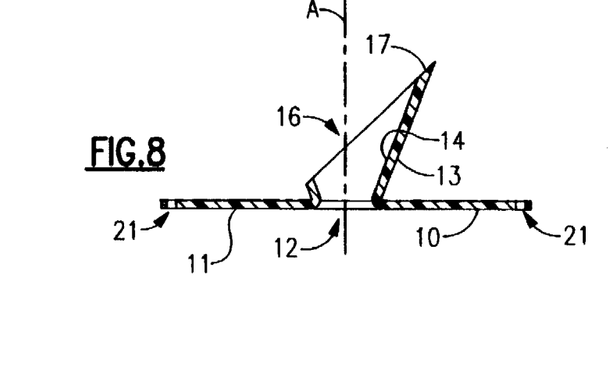
FIG. 8 is a cross-sectional view along section line 8—8 of FIG. 7.

The top wall 3 of the exterior housing 4 has a centrally located aperture 8 formed therein which, during use, is centered about the observation axis A. A frusto-conical side wall 6 extends from the top wall 3 of the exterior housing inwardly and downwardly along the observation axis A toward the object O to be observed. The side wall 6 is truncated by a plane P which extends obliquely, e.g. at a 45° angle, with respect to the observation axis A thereby forming an elliptical end surface 7 at the smaller diameter truncated end of the truncated frusto-conical side wall 6. The elliptical surface 7 of the exterior housing 4 supports a first surface of the beam splitter or partially reflective mirror 18. The exterior housing 4 can be manufactured from metal or may be molded from a plastic or some other synthetic or other suitable material. Preferably the exterior housing 4 is opaque.

The top wall 3 of the exterior housing is also provided with a wire aperture 9 (FIG. 6) which allows a fiber optic light source(s) to extend therethrough or an electrical cord to pass through the exterior housing and supply electrical power to the interior components of the exterior housing, e.g. the lights. A further detailed description concerning the supply of electrical power to the illumination source will follow hereinafter.

As previously indicated, the outer diffuser 10 covers the open end of the exterior housing 4 and is provided with a centrally located circular viewing aperture 12 which, when the outer diffuser 10 is attached to the housing 4, is aligned with the centrally located aperture 8 of the exterior housing. The outer diffuser 10 comprises a first planar ring shaped diffuser section 11 and a frusto-conical diffuser section 13. The ring-shaped diffuser 11 and the frusto-conical diffuser 13 are integrally formed with one another, e.g. they are molded as a unitary monolithic diffuser component from a translucent material such as DELRIN™, which is a thermoplastic polymer material sold by I.E. DuPont de Nemours & Company, Inc. Other suitable materials, which provide desired diffused illumination characteristics when illuminated by a light source, may also be employed. The exterior housing 4 is preferably manufactured from black colored DELRIN®.

The frusto-conical diffuser 13 extends from the ring-shaped diffuser 11 along the observation axis A toward the top wall 3. The ring-shaped diffuser 11 is truncated by the plane P which extends obliquely, e.g. at a 45° angle, with respect to the observation axis A thereby forming a second elliptical surface 17 at the larger diameter truncated end of the truncated frusto-conical diffuser 13. The elliptical surface 17 of the outer diffuser 10 supports a second opposed surface of the beam splitter or partially reflective mirror 18. The outer diffuser 10 must be transparent to allow diffused light to pass therethrough.

The outer diffuser 10 is provided with a plurality of screw holes 21, e.g. 4 holes, spaced about the perimeter of the outer diffuser 10 which are alignable with a plurality of tapped screw holes 19, e.g. 4 holes, provided in the side wall 5 of the exterior housing 4. The outer diffuser 10 is releasably secured to the exterior housing 4 via plurality of screws 20 passing through the screw holes 21 and threadingly engaging with the tapped screw holes 19. When the outer diffuser 10 is secured to the exterior housing 4, those two components define an interior cavity 22 which accommodates the internal components. It is to be appreciated that a variety of other known releasable attachment mechanisms, for attaching the outer diffuser 10 to the exterior housing 4, may be also employed.

An illumination source 24, such as a flexible LED circuit supported by a backing material, a ring light, fiber light, etc., is accommodated within the interior cavity 22 defined by the outer diffuser 10 and the exterior housing 4. The illumination source 24 is secured to the inner surface of the side wall 5 by a suitable fastening device (not shown), e.g. a screw(s), glue, etc.

In the embodiment shown in FIG. 2, in which the exterior housing of the illumination source 24 has a diameter of approximately 3 inches, the flexible circuit has a length of approximately 8.12 inches and a width of approximately 1 inch. A plurality of individual high intensity LEDs, e.g. 75, are supported along the length of the flexible illumination circuit and each of the individual LEDs is interconnected, via a plurality of wires (not shown in detail), to an electrical cord 28 which extends out of the exterior housing 4 through the wire aperture 9. The electrical cord 28 has a suitable electrical contact or plug 30, at a remote opposite end thereof, for facilitating connection of the illumination source 24 to an appropriate power supply. If desired, an inner cylindrical or partially cylindrical diffuser 26 can be positioned within the interior cavity 22 and located between the illumination source 24 and the second diffuser 14 to further assist with diffusing the light directed by the illumination source 24 toward the frusto-conical diffuser 13.

A suitable beam splitter 18, such as 0.010 inch half-silvered optical clear lucite member, is sandwiched, e.g. by compression, between the oval surface 7 of the housing and the oval surface 17 of the frusto-conical diffuser 13. The beam splitter 18 is typically secured to either one or both oval surfaces 7, 17 by glue or some other adhesive component. During use, the beam splitter 18 reflects a desired amount of light, e.g. between about 20% to 80% and preferably about 50%, which passes through the frusto-conical diffuser 13 along the observation axis A toward the object while allowing a desired amount of light, e.g. about 20% to 80% and preferably about 50%, reflected by the object to be observed to pass through the beam splitter 18 and be viewed by the observation device 1.

It is to be appreciated that the illumination source 24 is positioned to provide both illumination of the primary diffuser, i.e. the illumination source 24 illuminates a rear surface of the ring diffuser 11 to provide a primary source of illumination, as well as illumination of the secondary diffuser, i.e. the illumination source 24 illuminates a rear surface of frusto-conical diffuser 13 to provide diffused illumination along the observation axis.

Figure 1:
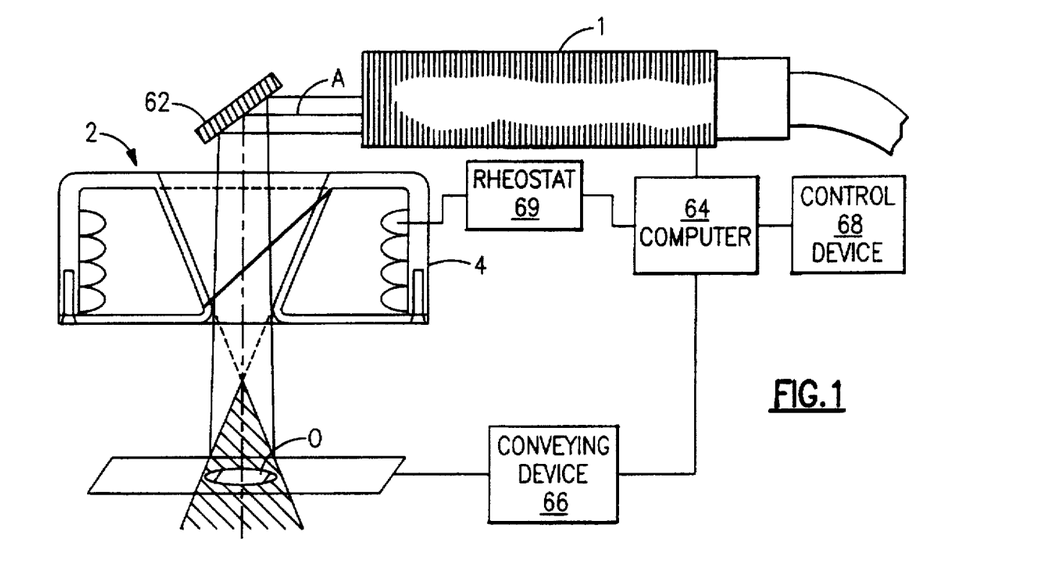
FIG. 1 is a diagrammatic view showing one embodiment for employing an observation device to view a desired object via the illumination device according to the present invention.

FIG. 1 shows one arrangement for using an observation device 1, such as a camera, for viewing an object O to be observed. The compact illumination device 2 is located at a desired distance, e.g. a few inches or so, above the object O to be observed and is provided with a single source of light 24 so that both direct primary diffused light and reflected secondary diffused light illuminate the object O. A mirror 62 is located at a desired distance above the opening 8 of the exterior housing 4 and arranged at a position of approximately 45° angle relative to the observation axis. The observation device 1 is positioned so that the image of the object passes through the beam splitter 18 and is reflected by the mirror 62 to a lens (not numbered) of the observation device 1 for viewing.

The observation device 1 communicates the sensed image to a computer 64 via suitable wiring or cabling. The computer 64, in turn, may be connected, via a suitable wiring or cabling, to a conveying apparatus or means 66 which conveys one of the illumination device 2 or the object O to be observed relative to the other. The computer 64 then transmits, via suitable wiring or cabling, the sensed image to a control device 68 which manipulates the information, as desired for one of accepting or rejecting the object O being observed, reproducing an image of the object O, or initiating any further desired manufacturing or inspection step required of the application at hand. As such teaching with respect to the above additional processing is well known in the art, a further detailed discussion concerning the same is now provided herein With reference now FIGS. 9–11, a second embodiment of the illumination device according to the present invention will now be discussed. This embodiment is similar to the previously discussed embodiment and includes an exterior housing 4 having a top wall 3 and a side wall 5. The outer diffuser 40 includes a centrally located circular diffuser aperture 42 as well as a ring shaped planar diffuser 44 and a truncated second diffuser 46, as with the first embodiment. The truncated surface 50 of the second diffuser 46 supports the beam splitter 18 which, due to the overall shape of the truncated second diffuser 46 as well as an inner contoured surface 52 of the exterior housing 4, the two members mate with one another to maintain the beam splitter 18 in a desired curved configuration.

Figure 10:
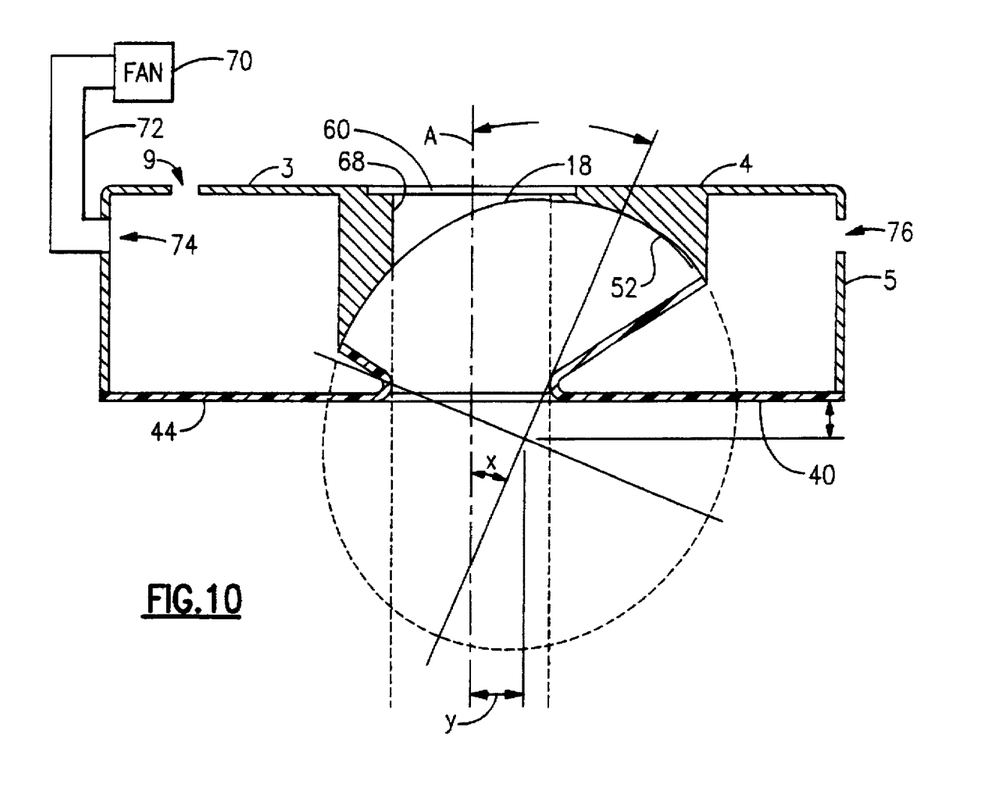
FIG. 10 shows the engagement between the first diffuser component and the exterior housing to maintain the curved beam splitter's configuration as well as the manner in which the curvature of the beam splitter is determined.
Figure 11:
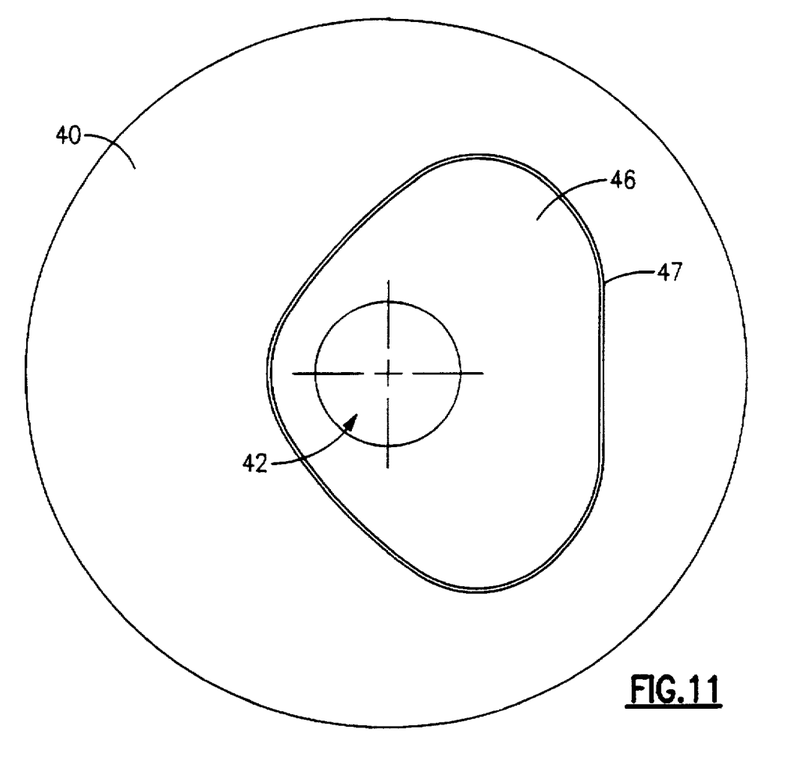
FIG. 11 is a top plan view of the modified diffuser component of FIG. 9.

The truncated surface 50 of the second diffuser 46 has an outer contour surface 47 which is somewhat oval in shape, as can be seen in FIG. 11 of the drawings. The inner contoured surface 52 supported by the exterior housing 4 is also contoured so that when the beam splitter 18 is sandwiched between the contour surface 47 of the second diffuser 46 and the inner contoured surface 52 of the exterior housing 4, the beam splitter 18 will be forced into a generally partial conical configuration and arrange to illuminate the object O with secondary diffused light. The term "conical", as used in this application, includes elliptical, spherical, cylindrical, egg-shaped or any other appropriated curved surface capable of directing light along the observation axis toward the object to be observed. One conical such configuration is shown in FIG. 10 of the drawings.

Figure 9:
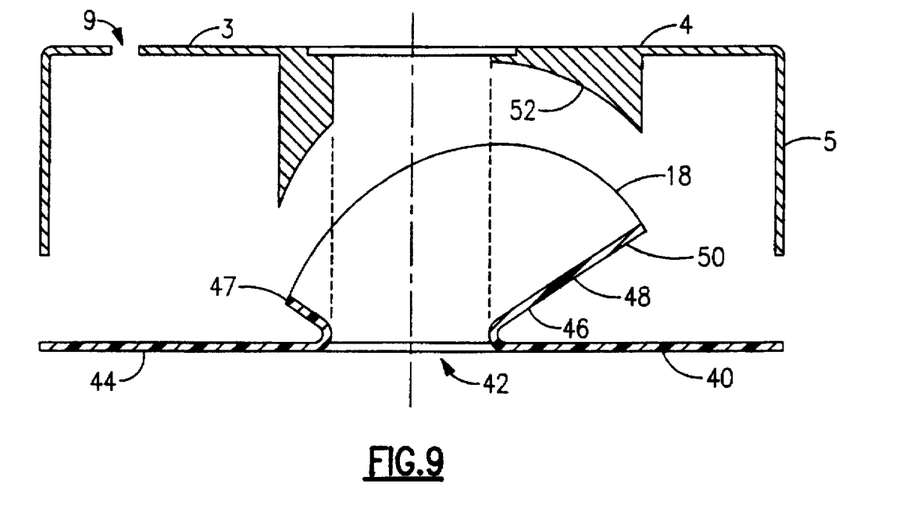
FIG. 9 is a diagrammatic cross-sectional view of a second embodiment of the illumination device according to the present invention employing a curved beam splitter.

According to the second embodiment, a transparent cover 60, of plastic, glass or the like (e.g. clear Lucite®, which is a material sold by I.E. DuPont de Nemours & Company, Inc.), is secured to and seals the centrally located aperture 8 of the exterior housing 4. The transparent cover 60 prevents dirt or other contaminants from coming into contact with the beam splitter 18.

The exterior housing includes a light absorbing panel, layer, coating or surface 68 located adjacent a rear surface of the beam splitter 18 to absorb diffused light which passes through the beam splitter. The intensity of the light generated by the light source 24 may be adjustable by a rheostat 69 to adjust the intensity and character of the light cast upon the object O. It is to be appreciated that the computer 64 (FIG. 1) can be coupled to the rheostat 69 for automatically adjusting the intensity and character of the light cast upon the object. As such teaching is well-known in the art, further detailed discussion concerning the same is not provided herein.

As can be seen in FIG. 10, a fan 70 may be connected with an inlet 74 of the exterior housing 4, via an air supply conduit 72. The exterior housing 4 is also provided with an exhaust air outlet 76 to discharge the air supplied to the interior of the illumination device via the fan 70. The purpose air supplied by the fan 70 is to cool the internal components of the illumination device, e.g. the light(s), and prevent overheating of the same. If desired, a grating, wire mesh or some other protective member may cover the exhaust outlet 76.

In the second embodiment shown in FIGS. 9–11, the exterior housing has an outer diameter of about 6.02 inches (152.8 mm), a height of 1.71 inches (43.5 mm), the central aperture has a width of 1.18 inches wide (30.00 mm), angle X is equal to 20.1 degrees and dimension Y is 0.49 inches (12.4 mm). In addition, the ellipse has a major radius of 1.86 inches (47.2 mm) and a minor radius of 1.60 inches (40.5 mm). Lastly, the center of the ellipse is located 0.23 inches (5.8 mm) below the outer diffuser 40. The ellipse is rotated about a central elongate axis to define the partially spherical shape to be occupied by the curved beam splitter 18.

Figure 12:
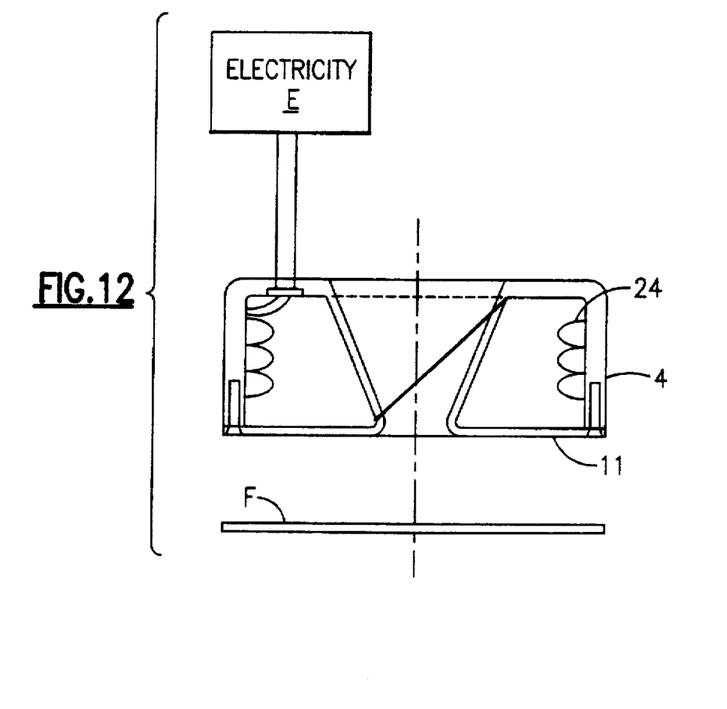
FIG. 12 is a diagrammatic view showing an arrangement for calibrating the outer diffuser is to ensure uniform illumination of a desired object via the illumination device.

Prior to the use or sale of the compact illumination device according to the present invention, the outer diffuser is calibrated to ensure uniformed illumination and a further discussion concerning the same is provided with reference to FIG. 12. This is achieved by connecting the illumination source 24 to a supply of electricity E and attaching the compact diffused illumination device 2 to suitable calibration equipment. Thereafter, the diffused light cast by the ring diffuser 11 illuminates a piece of photographic film F, or the like. In the event that cast light from the ring diffuser 11 provides uniformed illumination, the photographic film F will be uniformly illuminated over its entire surface area. If, however, the cast light from the ring diffuser 11 does not provide uniformed illumination of the photographic film F, i.e. one or more areas of the ring diffuser 11 allow more light to pass therethrough and/or one or more areas allow less light to pass therethrough, the photographic film will detect and reveal such nonuniform illumination. Thereafter, the exposed photographic film F or a reproduction of the photographic image printed on acetate is glued, pasted, secured, coated or applied on an inner surface of the ring diffuser 11 to mask the imperfections contained in the ring diffuser 11 so that, following calibration, a substantially uniformed illumination will be provided by the outer surface of the ring diffuser 11. Important feature of the above calibration technique is to alter or modify the outer diffuser so that when that diffuser is overlayed or coated with a semi-opaque pattern having a desired optical pattern, the outer diffuser provides a substantially uniform primary illumination of the object with diffused light.

It is to be appreciated that the area of the photographic film to be illuminated should be the same size as the ring diffuser 11 to facilitate applying the exposed photographic film or a reproduction of the photographic image to an inner surface of the ring diffuser 11 to mask the imperfections. Further, the photographic film and the ring diffuser 11 should have alignment indica to facilitate accurate aligned of those two components relative to one another. Such alignment and orientation must be maintained so that the photographic film or reproduction can be accurate applied to the inner surface of the ring diffuser 11 to provide the desired masking and uniform illumination.

The beam splitter 18 is typically 60/1000 of an inch thick and the opposed beam splitter surfaces are each conventionally provided with silvered strips, or otherwise treated, so that the beam splitter 18 constitutes both a reflective surface and a light pervious surface wherein light may pass through the beam splitter 18 from the object O for observation by the camera 1, and the beam splitter 18 also reflects the diffused light generated by the light source. Alternatively, the beam splitter 18 can be formed by a half silvered membrane pellicle of nitrocellulose or plastic material, such as "MYLAR", which has advantageous beam splitting characteristics in certain applications. Either material used as the beam splitter mirror 18 may be provided in a curved configuration having a concave face disposed towards both the object O and the light source 24 and a convex face disposed towards the observation means, such as a machine vision camera. This configuration provides an increased range of incident angles for the diffused light supplied along the observation axis while reducing the height of the light source 24.

The light diffusers may be formed of treated glass, plastic, or other light translucent material capable of evenly diffusing light cast upon the diffuser by the light source. The light sources may consist of a plurality of lamps, ring lights, incandescent bulbs, diodes, optical fibers or any other illumination source capable of generating a relatively uniform panel of light cast upon the diffuser and such diffused light illuminates the beam splitter 18 and is projected along the observation axis A toward the object. It will be appreciated that this light is coaxial with and coincides with the observation axis A. The size of the beam splitter 18 is such that the diffused light reflected therefrom along the axis is sufficient to completely occupy the observation window such that the window will be "filled" with the diffused light emitting from second diffuser and the light source. It will be understood that the light source and translucent light diffuser may be varied in size, shape and relative proximity to one another to create continuous uniform illumination across objects of different sizes or at different working distances.

Upon practicing the invention, a beam splitter similar to those shown in my co-pending application Ser. No. 07/750, 257 filed Aug. 27, 1991, now U.S. Pat. No. 5,187,611 may be employed. In the practice of the invention, control means permit accurate control and variation of the diffused light being generated and reflected by the beam splitter in order to equate the beam splitter projected light to that supplied by the primary diffused light source.

It is to be appreciated that the thickness and transparency of the primary and secondary diffusers can be manipulated and/or adjusted as desired to facilitate even illumination of the object to be observed. Such teaching, which is more clearly set forth in U.S. patent application Ser. No. 08/501, 213 filed Jul. 11, 1995, is incorporated herein by reference.

Turning now to FIGS. 13–17, a detailed description concerning a third embodiment of the present invention will now be provided concerning only the new features. In this embodiment, a video camera 77 is combined or integrated into the illumination device to form a compact integrated unit 78. The height of the illumination source is generally shown by bracket H and comprises the beam splitter 84, the height of the primary and secondary light source(s), the thickness of the primary diffuser as well an separating distance panel or member 93. The "height" of the illumination source, as referred to herein and in the appended claims, means the distance measured from a top or outer most surface of the beam splitter 84 to a bottom or lower most surface of the outer diffuser 92 when measured parallel to the observation axis A (see FIGS. 13 and 18).

Figure 13:
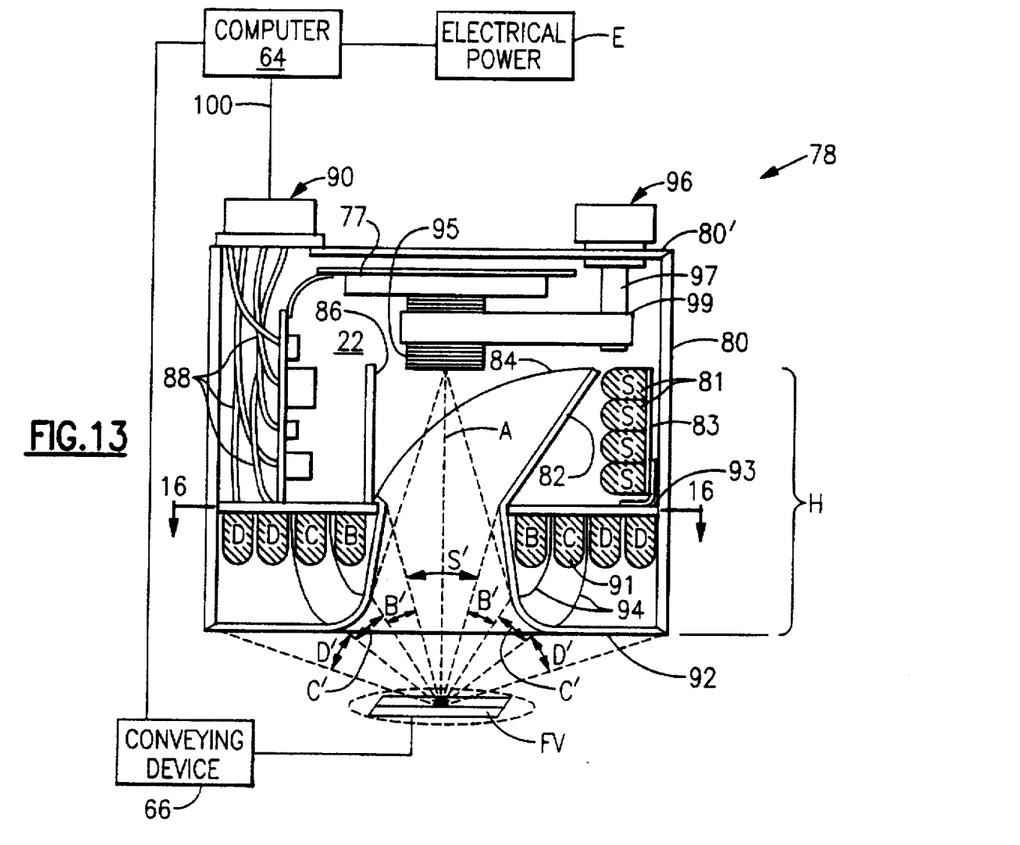
FIG. 13 is a diagrammatic cross-sectional view of a third embodiment of the illumination device, according to the present invention, which has an integrated video camera.
Figure 14:
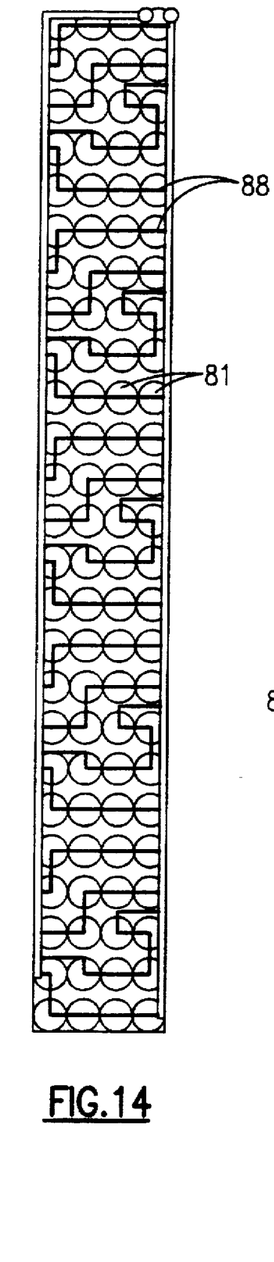
FIG. 14 is a front elevational view of an array of LEDs for providing diffused illumination along the observation axis.
Figure 15:
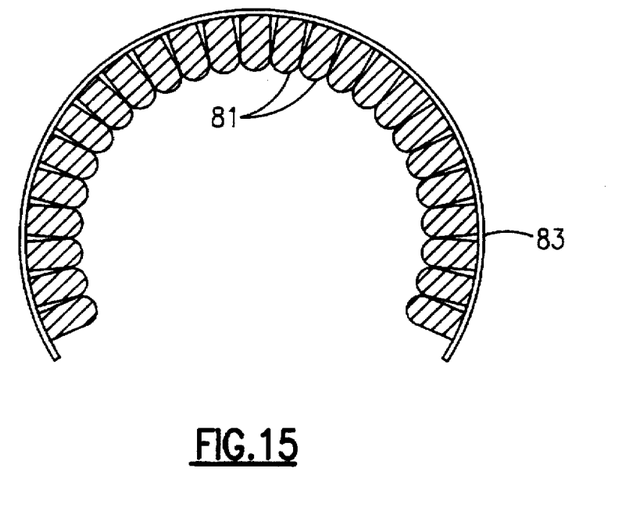
FIG. 15 is a plan view of the secondary diffused light when bent into its curved configuration.
Figure 16:
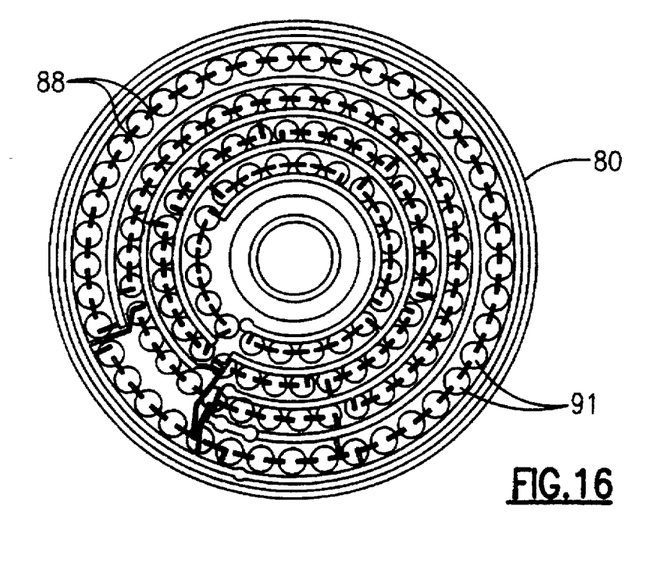
FIG. 16 is a diagrammatic cross-sectional view, along section line 16—16 of FIG. 13 showing an arrangement of the LEDs for providing primary diffused illumination.
Figure 17:
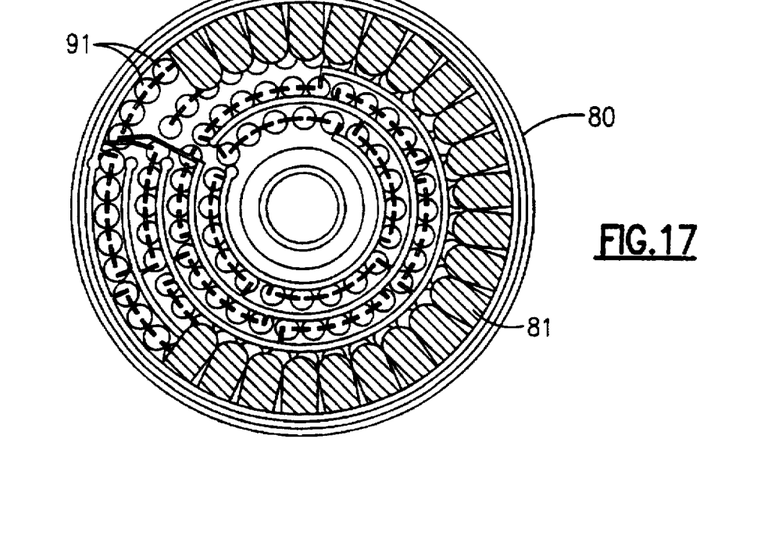
FIG. 17 is a diagrammatic top plan view of the primary and secondary light sources, with some of the components being removed for the sake of clarity, to show their interrelationship.

As with the previous embodiments, a partial circular secondary illumination source 81, e.g. a curved array of LEDs, is accommodated within the cavity 22 formed by the exterior housing 80, a top surface 80' of the housing and the outer diffuser 92. The secondary light source 81 is arranged to illuminate a rear surface of the frusto-conical diffuser 82 to provide diffused light to the curved beam splitter 84 so that a portion of the light is reflected along the observation axis (e.g. about 50% of the light is reflected by the beam splitter 84 while about 50% of the diffused light passes through the beam splitter 84 and is absorbed by the light trap 86 located adjacent but behind the beam splitter 84. In this embodiment, the beam splitter 84 is glued to the diffuser 82. The secondary illumination source 81 is supplied with electrical power via wires 88 to supply the illumination device with electrical power. An electrical power source E is coupled to an electrical connector 90, via an electrical cord 100, which in turn is coupled to the wires 88.

The primary light source 91 is arranged to provide primary illumination of the field-of-view FV. As can be seen in this embodiment, the primary light source 91 is divided or partitioned into three co-axially arranged primary illumination zones, labeled as B, C and D. A plurality of opaque, curved reflective baffles 94 are utilized to divide or segment the primary illumination source 91 into its co-axial arranged zones. Each illumination zone is positioned to direct or channel light over a portion of the outer diffuser 92 to provide illumination of the desired angle of incident of the field-of-view FV, e.g. illumination zones B, C, D and S, respectively, supply diffused light over angle of incident B', C', D' and S' as can be seen in FIG. 13. Each illumination zone B, C and D is electrically coupled to the wires 88 (not shown in detail) for supplying electrical power to the individual LEDs.

Figure 19:
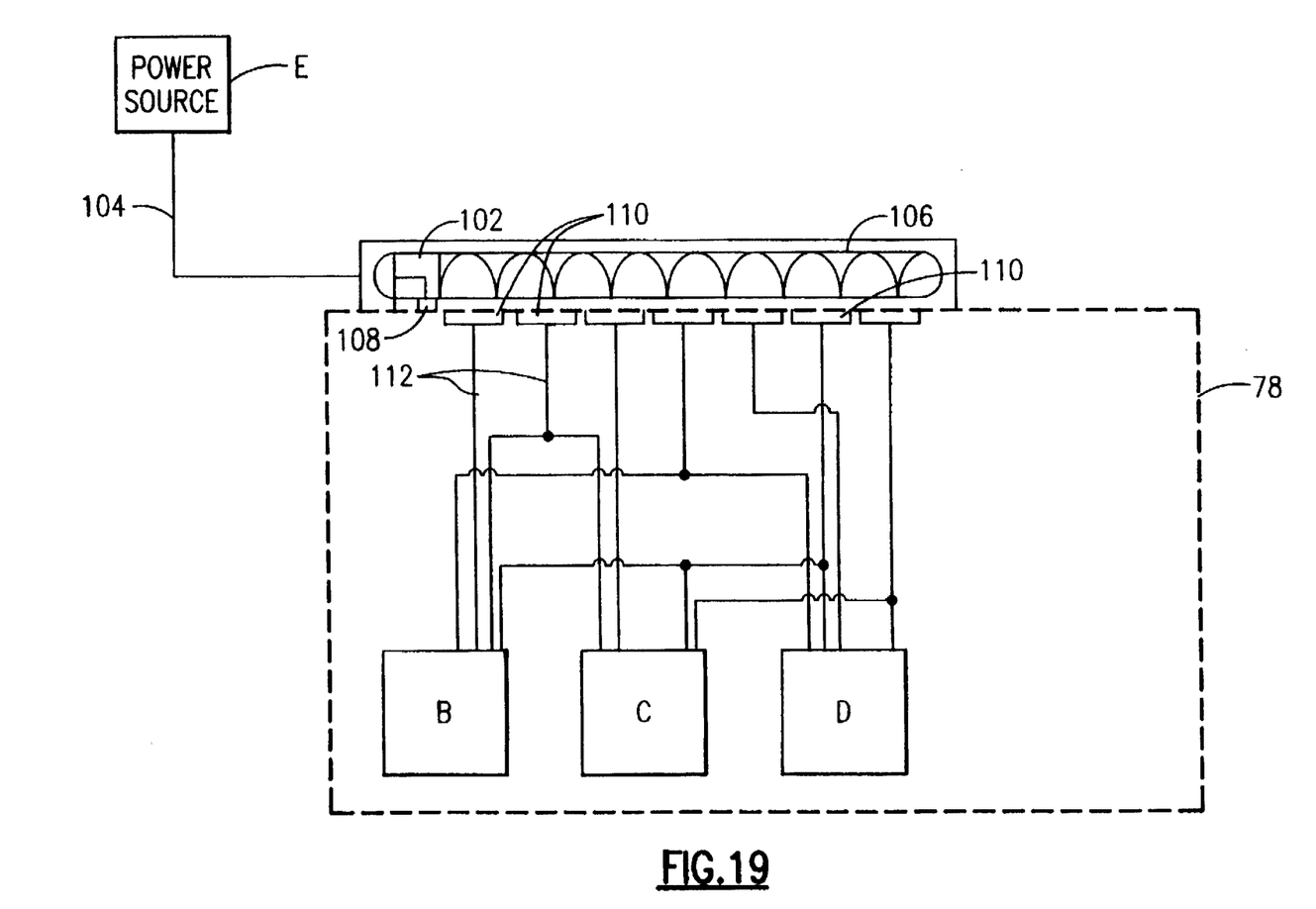
FIG. 19 is a diagrammatic representation of a triggering mechanism for automatically sequencing various combinations of illumination zones.

It is to be appreciated that the supply of electrical power to each illumination zone B, C and D of the primary illumination source 91 can be either manually controlled or, as shown in the embodiment of FIG. 13, be automatically controlled by a computer 64 or some other control device (FIG. 19). As with the previous embodiment, the computer 64 may be coupled to a conveying device 66 for providing relative movement between the compact unit 78 and the object to be observed. The illumination zone B, C, D and S can be operated separately from one another or in any desired combination to achieve a wide variety of illumination effects including "dark-field"0 illumination, "bright-field" illumination and continuous diffuse illumination. The computer 64 may be programmed, if desired, to automatically ascertain which combination of illumination zones, e.g. B, C, D and/or S, achieves optimum illumination of the object for any given application.

An opaque panel 93 separates the primary illumination source 81 from the remainder of the compact unit. The opaque panel 93 is provided with an opening which facilitates visual inspection of the object to be observed by the camera 77. The video camera 77 (e.g. a board-level video camera such as ULTRAK BC 460/P, for example) is supported, via a bracket or the like, adjacent the top inner surface 80' of the compact unit 78 and positioned to receive light reflected along the illumination axis A for viewing a desired portion of object located in the field-of-view FV. The video camera 77 is provided with an adjustable video camera lens 95. A camera focusing knob 96 is provided with a rotatable cylindrical member 97 which extends along and is located adjacent the lens 95. The cylindrical member 97 is coupled to the lens 95 via an endless rubber belt 99 or the like for facilitating focusing adjustment of the camera 77, i.e. any rotation of the focusing knob 96 causes rotation of the cylindrical member 97 which, in turn, transmits such rotation to the lens 95 via the endless belt 99. As such adjustment is well known in this art, a further detailed description concerning the same is not provided herein.

It is to be understood that this embodiment could be provided with a set of at least four separate rheostats for manually controlling the illumination characteristics of each of the four illumination zones B, C, D and S separately from one another. If desired, the number of illumination zones can be varied, i.e. increased or decreased, depending on the illumination application at hand.

Figure 18:
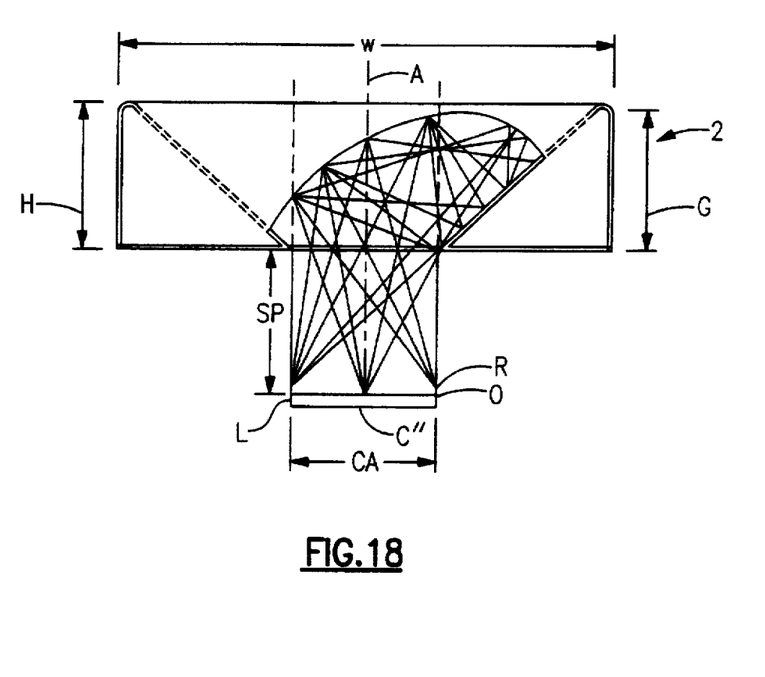
FIG. 18 is a diagrammatic cross-sectional view of a illumination device, according to the present invention, showing desired ray tracing to insure uniform illumination of the desired area to be observed by the illumination device.

With reference now to FIG. 18, a ray tracing diagram is shown for determining the necessary curvature of the beam splitter 84 for that application. As can be seen in that figure, the ray tracing paths for a left region L, a central region C" and a right R region of the object O to be observed are shown. As such ray tracing is well-known in the art, a further detailed description concerning the same is not provided herein.

The contour of the curved beam splitter is determined by such ray tracing and it will be appreciated that such contour depends upon the distance that the top surface of the object O is spaced SP from a bottom of the illumination device 2, the clear aperture dimension CA of the illumination device, the height H of the illumination device, etc. In this embodiment, the clear aperture CA, the spacing SP of the bottom portion of the illumination device from the object O to be observed, and the height H of the illumination device are all about equal, e.g. about 2.95 inches (74.9 mm) while the width of the housing is about three (3) times the clear aperture dimension. An important feature to bear in mind is that the second diffuser is not permitted in any way to provide direct illumination of the desired surface of the object O to be observed.

According to this invention, the height H of the illumination source is about three (3) times the minimum transverse dimension of the opening provided in the outer diffuser, preferrable about two (2) times the minimum transverse dimension of the opening provided in the outer diffuser, and most preferrable about one (1) times the minimum transverse dimension of the opening provided in the outer diffuser.

Turning now to FIG. 19, a detailed description concerning a triggering mechanism, for use in combination with the present invention, will now be provided. The integration unit 78, as with the previous embodiment, contains three illumination zones B, C and D as well as the other components shown in FIG. 13. For the sake of clarity, however, those components are not shown in detail in this Figure. The integrated unit 78 is additionally provided with a movable triggering mechanism 102 which is connected to a power source E via an electric cable or wire 104. The electric wire 104 must facilitate movement of the triggering mechanism 102 along an elongate slot 106 to supply electrical power thereto and allow the desired automatic sequencing of all of the possible combinations of illumination zones B, C and D. The triggering mechanism 102 is provided with an electrical contact 108, coupled to the electric wire 104, which is arranged to supply electrical power from the power source 100 to a desired one of the seven electrical contacts 110. As the trigger mechanism 102 is moved along the slot 106, the electric contact 108 engages with a desired one of the mating electrical contacts 110 and supplies electrical power thereto for a very short period of time, e.g. a fraction of a second. During such movement of the triggering mechanism 102, the electric contact 108 first supplies electrical power to the first electrical contact 110, then to the second electrical contact 110, then the third electrical contact 110, and so forth until all electrical contacts 110 have been separately supplied with electrical power.

As can be seen in FIG. 19, the first electrical contact 110 only supplies electrical power to illumination zone B; the second electrical contact 110 supplies electrical power to illumination zone B and C; the third electrical contact 110 supplies electrical power to only illumination zone C; the fourth electrical contact 110 supplies electrical power to illumination zones B and D; the fifth electrical contact 110 supplies electrical power to only illumination zone D; the sixth electrical contact 110 supplies electrical power to illumination zones B, C and D; and the seventh electrical contact 110 only supplies electrical power to illumination zone D. This triggering arrangement facilitates illumination of the object O to be observed by all possible illumination combinations of the illumination zones B, C and D by a hard wiring arrangement.

The observation device or camera 77 is coupled to the triggering mechanism so as to generate at least one image during each possible combination of the illumination zones, e.g. the observation device generates at least seven images, so that the integrated unit 78 can then employ that information as desired. If the integrated unit 78 is also equipped with a computer, the computer can be coupled with the triggering mechanism and the observation device to determine which illumination combination provides the best image of the object to be observed and employ that image for further processing. As such feature is well known to those skilled in this art, a further detail description concerning the same is not provided herein.

It is to be appreciated that the triggering mechanism 102 can be biased into the position shown in FIG. 19, by a (compression) spring 114 or some other biasing means, so that the triggering mechanism 102 is returned an original position ready for a further illumination cycle. The arrangement shown in FIG. 19 is particularly suitable for a hand-held scanning device for scanning bar code information off various items and products. The operator would position the object O along the observation axis A and merely slide, move, squeeze, pull or otherwise actuate the trigger mechanism 102 to traverse the trigger along the slot 106 and then release the trigger 102 at the end of the slot thereby allowing the spring 114 to return the trigger mechanism 102 back to its originally position for further scanning.

If desired, the trigger mechanism can be biased or forced against the electrical contacts 110 to insure that a good electrical connection between the contacts 108 and 110 is achieved.

Figure 20:
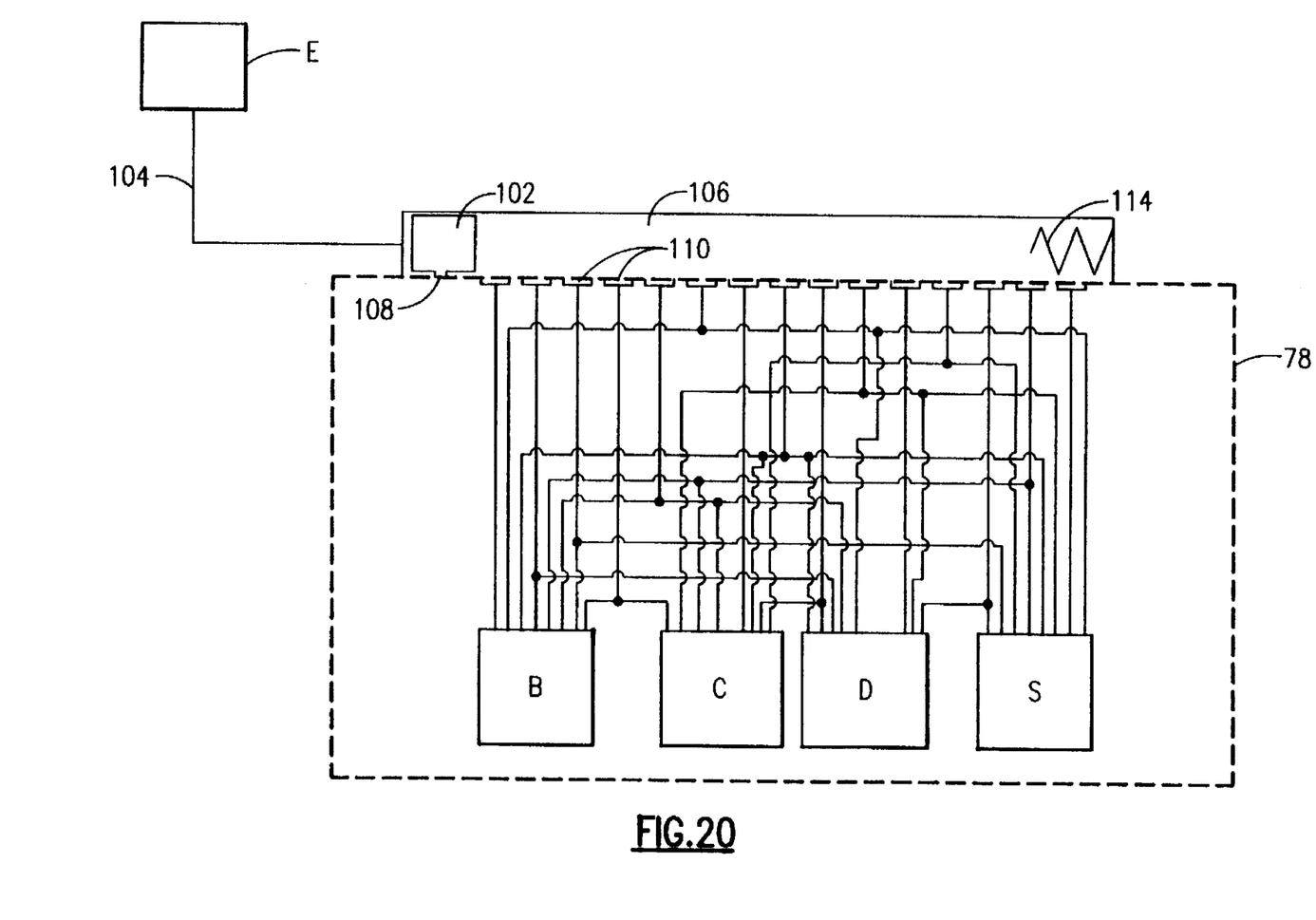
FIG. 20 is a diagrammatic representation of a second triggering mechanism for automatically sequencing various combinations of illumination zones.

Turning now to FIG. 20, a brief description concerning a second triggering mechanism, for use in combination with the present invention, will now be provided. The integration unit 78 contains four illumination zones B, C, D and S as well as the other components shown in FIG. 13. For the sake of clarity, however, those components are not shown in detail in this Figure. The integrated unit 78 is also provided with a movable triggering mechanism 102, as with the previous embodiment, as well as fifteen electrical contacts 110 each hard wire for one of fifteen possible illumination combinations. As the trigger mechanism 102 is moved along the slot 106, the electric contact 108 engages with a desired one of the mating electrical contacts 110 and supplies electrical power thereto for a very short period of time, e.g. a fraction of a second. During such movement of the triggering mechanism 102, the electric contact 108 first supplies electrical power to the first electrical contact 110, then to the second electrical contact 110, then the third electrical contact 110, and so forth until all fifteen electrical contacts 110 have been separately supplied with electrical power.

It is to be appreciated that a variety of different arrangements could be utilized to achieved the desired mechanical illumination combinations of the various illumination zone B, C, D and/or S. It is intended that all such modification would be readily apparent one skilled in this art and thus are to be considered within the scope of this invention.

If height is not a critical feature for a given application, it is to be appreciated that the position of the secondary light source S and the diffuser can be switched with that of the observation device 1 so that the beam splitter would allow diffuse secondary light to pass therethrough and reflect light reflected from the object to the lens.

Since certain changes may be made in the above described illumination device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

I claim:

1. A compact diffuse illumination device for evenly illuminating a desired portion of an object when observed along an observing axis extending through an object observing location, said compact diffuse illumination device comprising:

at least a light source for providing light;

a first diffuser surface, for supplying a primary diffused light, defining an opening through which the observing axis passes, said first diffuser surface being arranged to receive light from said light source and supply said primary diffused light to provide even illumination of the desired portion of the object, when placed at the observing location and viewed along said observing axis, except for a portion of the object effected by the opening;

a second diffuser arranged to receive light from said light source and supply secondary diffused light to illuminate a desired portion of the object effected by the opening; and a partially reflective mirror being arranged along said observing axis to receive and reflect at least a portion of said secondary diffused light, supplied by said second diffuser, along the observing axis to evenly illuminate each portion of the object effected by the opening to produce, when said primary diffused light illuminates said object, even illumination of the object when viewed along the observing axis;

wherein said opening defines a clear aperture of the diffuse illumination device and a height of said light source is no greater than about three times a dimension of said clear aperture.

2. A compact diffuse illumination device according to claim 1, wherein said illumination device includes an exterior housing connected to said first diffuser surface, and said exterior housing and said first diffuser surface define a cavity accommodating said light source.

3. A compact diffuse illumination device according to claim 2, wherein an observation passage is formed and extends through both said exterior housing and said first diffuser surface for facilitating viewing of said object to be observed along said observation axis.

4. A compact diffuse illumination device according to claim 3, wherein said first diffuser surface supports said second diffuser which cooperates with said light source for supplying said secondary diffused light to said partially reflective mirror.

5. A compact diffuse illumination device according to claim 4, wherein said first diffuser surface and said second diffuser are formed as a single monolithic component.

6. A compact diffuse illumination device according to claim 3, wherein said observation passage is defined by a frusto-conical wall and said exterior housing defines a first portion of the frusto-conical wall and said second diffuser defines a second portion of said frusto-conical wall and said partially reflective mirror is located between said first and second portions.

7. A compact diffuse illumination device according to claim 3, wherein an opening is formed in said exterior housing and said opening in said exterior housing is larger in size than said opening provided in said first diffuser surface.

8. A compact diffuse illumination device according to claim 3, wherein the exterior housing is provided with at least one further opening, and an electrical cord extends through said further opening and is connected to said light source to supply electrical power thereto.

9. A compact diffuse illumination device according to claim 2, wherein said exterior housing is opaque and said first diffuser surface is transparent.

10. A compact diffuse illumination device according to claim 2, wherein said illumination device occupies a volume of no greater than about 16 cubic inches.

11. A compact diffuse illumination device according to claim 2, wherein said light source is a flexible LED circuit accommodated within said cavity.

12. A compact diffuse illumination device according to claim 2, wherein said first diffuser surface is releasably fastened by at least one member to an open end of said exterior housing.

13. A compact diffuse illumination device according to claim 2, wherein said exterior housing is provided with an inlet opening and an outlet opening and a fan is connected to one of said inlet opening and said outlet opening for supplying cooling air to internal components of said illumination device while other of said openings facilitates exhausting of said cooling air from said illumination device.

14. A compact diffuse illumination device according to claim 2, wherein said second diffuser is located between said light source and said partially reflective mirror, and an intermediate diffuser is positioned within said cavity, between said light source and said second diffuser, to assist with further diffusion of light supplied by said light source to said second diffuser.

15. A compact diffuse illumination device according to claim 2, wherein a surface of said first diffuser surface supports a calibration mechanism to facilitate uniform illumination by said first diffuser surface.

16. A compact diffuse illumination device according to claim 2, wherein said first diffuser surface supports said second diffuser, and an inner surface of said exterior housing and an outer surface of said second diffuser are contoured so that, when said exterior housing is mated with said second diffuser, said partially reflective mirror between said exterior housing and said second diffuser is biased into a partially spherical configuration.

17. A compact diffuse illumination device according to claim 1, wherein said first diffuse surface is a ring shaped planar member which has said opening centrally formed therein.

18. A compact diffuse illumination device according to claim 1, wherein said light source comprises:

a primary light source, cooperating with said first diffuser surface, for supplying said primary diffused light to said object to be observed; and a secondary light source, cooperating with said second diffuser for, supplying said secondary diffused light to said object to be observed.

19. A compact diffuse illumination device according to claim 1, in combination with an observation device, a computer, containing a central processing unit, and a conveying apparatus for moving one of said compact diffuse illumination device and the object to be observed relative to one another, and said computer is connected with said observation device and said conveying apparatus for sensing and outputting a sensed image of the object being observed to control manipulation, via said conveying apparatus, of the object being observed.

20. A method of evenly illuminating a desired portion of an object to be observed, when observed along an observing axis extending through an object observing location, via a compact diffuse illumination device, said method comprising the steps of:

provid­ing a light source for supplying light;

defining an opening in a first diffuser surface, for supplying a primary diffused light, through which the observing axis passes, and arranging said first diffuser surface to received light from said light source and supply said primary diffused light to provide even illumination of the desired portion of the object, when placed at the observing location and viewed along said observing axis, except for a portion of the object effected by the opening;

supplying secondary diffused light, via a second diffuser, to illuminate a desired portion of the object effected by the opening;

arranging a partially reflective mirror along said observing axis to receive and reflect at least a portion of said secondary diffused light, supplied by second diffuser, along the observing axis to evenly illuminate each portion of the object effected by the opening to produce, when said primary diffused light illuminates said object, even illumination of the object when viewed along the observing axis;

defining, said opening, a clear aperture of the diffuse illumination device; and providing said light source with a height which is no greater than about three times a dimension of said clear aperture.

* * * * *